US008347746B2

(12) United States Patent
Hafenrichter et al.

(10) Patent No.: US 8,347,746 B2
(45) Date of Patent: Jan. 8, 2013

(54) CRAWLING AUTOMATED SCANNER FOR NON-DESTRUCTIVE INSPECTION OF AEROSPACE STRUCTURAL ELEMENTS

(75) Inventors: Joseph L. Hafenrichter, Seattle, WA (US); Gary E. Georgeson, Federal Way, WA (US); Nancy L. Wood, Clayton, MO (US)

(73) Assignee: The Boeing Company, Chicago, IL (US)

( * ) Notice: Subject to any disclaimer, the term of this patent is extended or adjusted under 35 U.S.C. 154(b) by 242 days.

(21) Appl. No.: 12/657,424

(22) Filed: Jan. 19, 2010

(65) Prior Publication Data

US 2011/0178727 A1 Jul. 21, 2011

(51) Int. Cl.
*G01D 21/00* (2006.01)
(52) U.S. Cl. ...................................... 73/866.5; 73/865.8
(58) Field of Classification Search .................. 73/866.5, 73/865.8
See application file for complete search history.

(56) References Cited

U.S. PATENT DOCUMENTS

| | | | |
|---|---|---|---|
| 4,146,967 A | 4/1979 | Rohner et al. | |
| 5,031,458 A * | 7/1991 | Young et al. ..................... | 73/636 |
| 5,698,787 A | 12/1997 | Parzuchowski et al. | |
| 6,220,099 B1 * | 4/2001 | Marti et al. ..................... | 73/633 |
| 6,829,959 B2 | 12/2004 | Gifford et al. | |
| 7,231,826 B2 | 6/2007 | Bossi et al. | |
| 7,240,556 B2 | 7/2007 | Georgeson et al. | |
| 7,315,609 B2 | 1/2008 | Safai et al. | |
| 7,337,673 B2 | 3/2008 | Kennedy et al. | |
| 7,562,593 B2 | 7/2009 | Engelbart et al. | |
| 7,640,811 B2 | 1/2010 | Kennedy et al. | |
| 2006/0043303 A1 | 3/2006 | Safai et al. | |
| 2009/0038398 A1 * | 2/2009 | Lavoie et al. ..................... | 73/637 |

OTHER PUBLICATIONS

European Search Report for application No. 11151274.5; May 31, 2011; 4 pages.
Defense, Space & Security; http://www.boeing.com.defense-space/support/maintenance/commercial/maus.html; 4 pages.

* cited by examiner

*Primary Examiner* — Hezron E Williams
*Assistant Examiner* — Nathaniel Kolb
(74) *Attorney, Agent, or Firm* — Armstrong Teasdale LLP (57) ABSTRACT

Apparatus for non-destructive inspection of structural elements or workpieces, in particular those having an airfoil configuration, that moves a scanning sensor across the width (span) of a structural element or workpiece for the purpose of detecting structural damage. In one embodiment, the apparatus simultaneously traverses the length (chord) of the structural element or workpiece. In another embodiment, the apparatus includes a guide rail that encompasses the structural element or workpiece and the scanning sensor travels along the guide rail from a first location at an upper rear region, to the front, of the structural element or workpiece, and then around the leading edge toward the lower rear region. The apparatus includes a processor and a display device to display the processed, sensed, information.

19 Claims, 5 Drawing Sheets

FIG. 5
Section A-A

CRAWLING AUTOMATED SCANNER FOR NON-DESTRUCTIVE INSPECTION OF AEROSPACE STRUCTURAL ELEMENTS

FIELD OF THE DISCLOSURE

The present disclosure relates generally to the field of non-destructive inspection of aerospace structural elements, and more particularly to a non-destructive inspection apparatus that mounts to, and travels along, an aerospace structural element, such as a rotorcraft blade, an aircraft propeller, winglets, a projectile fin, an aircraft tail section, a windmill blade, etc., while inspecting and determining the existence of structural defects and/or damage.

Non-destructive testing of structures involves thoroughly examining a structure without harming the structure or requiring significant disassembly of the structure. Non-destructive testing is advantageous for many applications in which a thorough inspection of the exterior and/or interior of a structure is required. For example, non-destructive testing is commonly utilized in the aircraft industry to inspect aircraft structures for any type of internal or external damage to the structure. Metallic aircraft structures are typically inspected for corrosion and/or cracking, particularly near fastener in the structure. Composite structures used in aerospace and other industries are typically inspected for any type of damage occurring anywhere on or within the composite material, including but not limited to delamination, erosion, impact damage, water ingression, disbands, inclusions, porosity, and cracking.

Various types of sensors may be utilized to perform non-destructive testing. One or more sensors may move over the portion of the structure to be examined, and receive data regarding the structure. For example, a pulse-echo, thru-transmission, or shear wave sensor may be utilized to obtain ultrasonic data, such as thickness gauging, detection of laminar defects and porosity, and/or crack detection in the structure. Resonance, pitch/catch or mechanical impedance sensors may be utilized to provide indications of voids or porosity, such as in adhesive bondlines of the structure. In addition, single and dual eddy current sensors impart and detect eddy currents within a structure so as to identify cracks and/or corrosion, particularly in metallic and other conductive structures. The data acquired by the sensors is typically processed by a processing element, and the processed data may be presented to a user via a display.

In many cases, structures must be inspected in the field because it is either not feasible or too expensive and time-consuming to transport the structure to an off-site laboratory for the inspection. For routine field inspections of structures, technicians typically manually scan the structures with an appropriate sensor. The manual scanning generally consists of a trained technician holding a sensor and moving the sensor along the structure to ensure the sensor is capable of testing all desired portions of the structure. In many situations, the technician must repeatedly move the sensor in the chordwise direction while simultaneously indexing the sensor approximately one-tenth of an inch in the spanwise direction. Alternatively, the technician can repeatedly move the sensor spanwise while simultaneously indexing the sensor approximately one-tenth of an inch in the chordwise direction. In addition, because the sensorsd typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician and interpreting the displayed data. Thus, manual scanning of structures is time-consuming, labor-intensive, and prone to human error. Furthermore, manual scanning may cause fatigue and/or other health problems for technicians, such as Repetitive Motion Disorders.

Automated inspection systems for routine field inspections, such as the Mobile Automated Scanner (M.A.U.S.), developed by the Boeing Company, provide automated data acquisition in a portable package for on-site inspections. One type of M.A.U.S. system automatically moves along the structure being evaluated via a linear track with vacuum controlled suction cups, another system includes handheld sensors and an associated manually movable slider, and still another employs tracks on which the scanning system moves. The M.A.U.S. system not only scans the structure, but also processes the data regarding the structure, and associates the data with the exact location on the structure from where the data was obtained.

While the M.A.U.S. system is portable, provides fast inspection rates, and employs numerous types of sensors, such as those mentioned above, the linear track on which it moves limits its use to structures where the track can mount to the structure and not interfere with the inspection area. Where its linear track attaches to the structure, the region underneath the track cannot be inspected during a scanning pass. The M.A.U.S. system is not adaptable to shorter chordlength aerospace airfoil structures, such as rotorcraft blades, aircraft propellers, smaller winglets, narrow tail sections, and windmill blades. Thus, it may not be feasible to use the M.A.U.S. system for shorter chordlength aerospace airfoil structures.

The M.A.U.S. also cannot do through-transmission ultrasonic inspection, so structure that requires this modality, such as some honeycomb structure, cannot be inspected using it. Airfoil structures are typically made with various laminate, honeycomb, foam, metal and/or composite skins. During flight operations, damage can occur in these structures due to impact, moisture damage, sand erosion or degradation. Indications of damage will provide sufficient justification to immediately remove the airfoil for inspection, and if needed, repair the structure.

Rotorcraft maintenance is a cumbersome endeavor for military and commercial operators. It has been said that there is a 10:1 ratio of maintenance man-hours to operations hours for typical rotorcraft. Currently, the operators often use the rudimentary tap test (coin or hammer) or hand-held NDI scanning devices to discern damage in the blades. But tap testing is crude and highly operator dependent such that many blades are dismantled and repaired when they are acceptable for continued use, and worse yet, some blades are passed that aren't flight worthy. Tap testing is also very slow and manually intensive, does not provide any images of the damage or a permanent record that can be stored, printed or sent electronically to a remote expert to be evaluated. Likewise, hand held NDI scanning devices are limited by operator skill as was discussed previously.

Another technique for assessing the condition of airfoil structures is automated scanning (among which the MAUS is a sub-set), but this type of requires tracks or other mounts, the devices used are not expandable, and they cannot scan leading edges or highly contoured areas. Nor are they capable of through-transmission inspection, and may require the structure to be removed in order for it to be inspected.

It would therefore be highly desirable to have an automated station or apparatus that would accurately determine the level of damage in airfoil structures, such as rotorcraft blades, and eliminating the removal for inspection of these types airfoil structures would be an even bigger benefit.

SUMMARY OF THE DISCLOSURE

In one aspect of the disclosure, an apparatus for providing an automated movement of a non-destructive inspection (NDI) sensor over a workpiece surface, includes a housing having forward and rear portions engaging opposing edges of the workpiece and an elongate member interconnecting the forward and rear portions of the housing, a biasing mechanism interacting with an end portion of the elongate member to urge the forward and rear portions toward one another to cause the workpiece to be securely held therebetween, an arm coupled to the housing for reversible movement in a first direction along the length of the elongate member and between the forward and rear portions of the housing, the arm supporting the NDI sensor, and a drive mechanism carried by said housing for moving the housing in a second direction perpendicular to the first direction over the workpiece, the drive mechanism including at least one friction element engaging a leading edge of the workpiece and a motor supported by the housing for driving the friction element along the one surface. The workpiece comprises an element having an airfoil configuration, and the housing further includes a sensor mechanism arranged at the leading edge of the workpiece for making sensing engagement therewith. The sensor mechanism arranged at the leading edge of the workpiece comprises an array of sensing elements supported for conformal engagement with the leading edge of the workpiece. The housing is disposed atop one major surface of the workpiece, and further includes a guide rod mounted to the forward portion, and a slider element slidably engaged with the guide rod for sliding movement therealong, the arm being pivotably coupled to the slider element. An encoder wheel is carried by the rear portion of the housing and has a portion engagable with the trailing edge of the workpiece, the encoder wheel transferring the biasing force to the workpiece trailing edge. The encoder wheel determines the spanwise position of the apparatus on the workpiece. The apparatus further includes a processor mechanism for analyzing data acquired by the NDI sensor and a display device for visually presenting the analyzed data.

In another aspect of the disclosure, an apparatus for providing an automated movement of a non-destructive inspection (NDI) sensor about the upper and lower surfaces of a workpiece with a single continuous motion includes an upper housing and a lower housing, each housing having forward and rear portions engaging opposing edges of the workpiece, and an elongate member interconnecting the forward and rear portions, a biasing mechanism interacting with an end portion of the elongate member to urge the forward and rear portions toward one another to cause the workpiece to be securely held therebetween, a drive mechanism carried by at least one of the housings for moving the apparatus in a spanwise direction over the workpiece, the drive mechanism including at least one friction element engaging a leading edge of the workpiece and a motor supported by at least one of the housings for driving the friction element along one of the upper or lower surfaces, an elongated guide rod encircling the upper and lower surfaces of the workpiece and being secured to at least one of the housings, a slider element coupled to the guide rod and movable therealong, and driver apparatus for moving the slider element along the guide rod. The forward portions of the upper and lower housings are both connected to the drive mechanism. The apparatus further includes an NDI sensor engaging a surface of the workpiece and an elongate arm connected between and to the NDI sensor and the slider element, the NDI sensor being moved along the upper and lower surfaces of the workpiece in a chordwise direction. The NDI sensor comprises at least one of a pulse-echo sensor, a shear wave sensor, a resonance sensor, a mechanical impedance sensor, and an eddy current sensor. The workpiece comprises an element having an airfoil configuration.

In yet another aspect of the disclosure, an apparatus for providing simultaneous non-destructive inspection (NDI) of upper and lower surfaces of a workpiece includes an upper housing and a lower housing, each housing including forward and rear portions engaging opposing edges of the workpiece, and an elongate member connecting the forward and rear housing portions, a biasing mechanism interacting with an end of the elongate member to urge the forward and rear portions toward one another to hold the workpiece securely therebetween, a drive mechanism for moving the housing in a spanwise direction over the workpiece, the drive mechanism including a friction element engaging a leading edge surface of the workpiece and a motor for driving the friction element along the edge surface, a guide rail mounted to a portion of the housing and extending in a chordwise direction, an NDI sensor element that is coupled to the guide rail for movement in the chordwise direction, and motion imparting apparatus for moving the NDI sensor element over the respective surface of the workpiece, motor apparatus for driving each of the upper and lower housings over a respective surface of the workpiece, and coupling apparatus for coupling the upper and lower housings together so that the upper and lower housings move simultaneously chordwise over the upper and lower workpiece surfaces. The NDI sensor comprises at least one of a pulse-echo sensor, a thru-transmission sensor, a shear wave sensor, a resonance sensor, a mechanical impedance sensor, and an eddy current sensor. Each of the upper and lower housings include a follower mechanism engaged with the trailing edge of the workpiece, the follower mechanism containing an encoding device to determine the spanwise location of the apparatus on the workpiece. The apparatus further includes a processor mechanism for analyzing data acquired by the NDI sensor, and a display device for visually presenting the analyzed data. At least one of the upper and lower housings further includes an encoder wheel supported from the rear portion thereof, the encoder wheel being urged into engagement with the trailing edge of the workpiece in order to determine the spanwise position of the apparatus as it moves along the workpiece. A sensor mechanism is arranged at the leading edge of the workpiece and makes engagement therewith. The sensor mechanism comprises an array of NDI sensing elements and a flexible member to which the elements are mounted, the elements being supported by the flexible member for conformal engagement with the leading edge of the workpiece.

Further aspects of the inspection apparatus and the method of using the apparatus are disclosed herein. The features as discussed above, as well as other features and advantages of the present disclosure will be appreciated and understood by those skilled in the art from the following detailed description and drawings.

DETAILED DESCRIPTION OF THE DISCLOSURE

Embodiments of the present disclosure now will be described more fully hereinafter with reference to the accompanying drawings. However, many different embodiments are contemplated and the present disclosure should not be construed as limited to the embodiments set forth herein; rather, these embodiments are provided so that this disclosure will be thorough and complete and better convey the scope of the disclosure to those skilled in the art.

In its broadest sense, this disclosure presents an autonomous, self-propelled, expandable, and adjustable apparatus for inspecting in-service aerospace structures such as rotorcraft blades, aircraft propellers, smaller winglets, narrow tail sections, and windmill blades for structural damage by "crawling along the length of the structure using the structure itself as the track, and employing scanning sensor mechanisms such as ultrasonic pulse echo, eddy current arrays, resonance arrays, and bondtester or laser probes, to access the conditions found as the inspection apparatus moves across the surface. Multiplexed pulser/receiver cards, and a controller within a computer with imaging software, can be cabled to the expandable crawler portion of the system to collect, display, and store NDI data.

Figure 1:
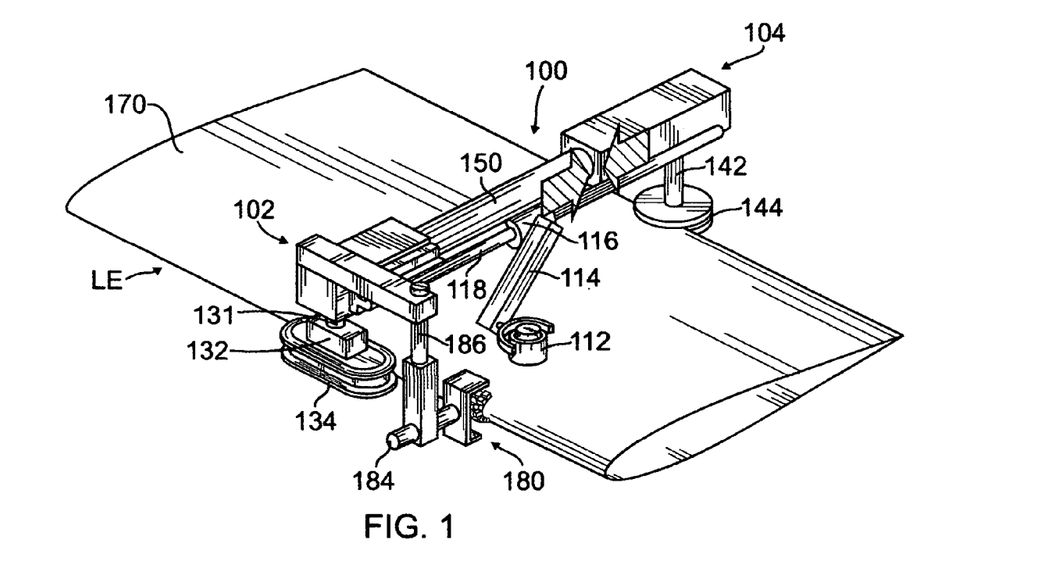
FIG. 1 is a perspective view of an inspection apparatus 100 mounted on an airfoil structure in accordance with a first aspect of the present disclosure.

As seen in FIG. 1, the inspection apparatus 100 includes a forward body part 102, a rear body part 104, and an "intercostals" element 150 that interconnects and secures the forward and rear body parts. The forward body part is positioned at a forward edge of the structural element 170 that is to be inspected, and the rear body part is positioned at an opposing edge of the structure to be inspected. Inspection of the structural element 170 is carried out, in part, by a face-sheet scanner 112 pivotally supported on an arm 114 mounted to a slider 116 carried on a guide rod 118. Contained within the face-sheet scanner 112 would be any one of a variety of NDI sensors to perform inspection of the structural element as described previously.

The forward body part has a first rod 131 depending therefrom on which is mounted a control motor 132. A drive track 134 is operatively connected to and supported from the control motor 132, the latter causing the drive track 134 to rotate about a rod 141 depending from the control motor as the drive track engages the leading edge of the structural element 170. A second rod 142 depends from the rear body part and carries a follower encoder wheel 144 on the free end thereof.

The drive track 134 and the encoder wheel 144 are held against, and in frictional engagement with, the leading and trailing edges, respectively, of the structure to be inspected. This is accomplished by a compressive force (see facing arrows in FIG. 1) imparted to the forward and rear body parts (to be discussed below). Preferably, the drive track is made of a material that frictionally engages the leading edge of the structural part being inspected so as to impart a driving force that moves the inspection apparatus 100 spanwise along the structural element 170. Additionally, the encoder wheel 144 tracks the linear position of the inspection apparatus 100 as it translates along the structural element 170. The forward body part 102 also carries a leading edge scanner assembly 180 that supports a leading edge sensor array 181 (see FIGS. 6 and 7 and the accompanying discussion).

Various types of sensors may be utilized to perform non-destructive testing. One or more sensors may move over the portion of the structure to be examined, and receive data regarding the structure. For example, a pulse-echo, thru-transmission, or shear wave sensor may be utilized to obtain ultrasonic data, such as thickness gauging, detection of laminar defects and porosity, and/or crack detection in the structure. Resonance, pitch/catch or mechanical impedance sensors may be utilized to provide indications of voids or porosity, such as in adhesive bondlines of the structure. In addition, single and dual current eddy current sensors impart and detect eddy currents within a structure so as to identify cracks and/or corrosion, particularly in metallic or other conductive structures. The data acquired by the sensors is typically processed by a processing element, and the processed data may be presented to a user via a display.

The rear body part 104 carries an encoder wheel 144 which depends from, and is attached to, the rear body part on a reversibly telescoping rod 142. The encoder wheel 144 applies a compressive force necessary to keep the inspection apparatus 100 aligned with the leading and trailing edges of the structural element 170. The compressive force is generated by an internal spring or compression generating mechanism (not shown) contained within the rear body part 104, engaging both the rear body part and the "intercostal" element 150 of the apparatus 100.

Inside the leading edge scanner assembly 180 (see FIGS. 3, 6, and 7), the leading edge sensor array 181 is conformably supported by the leading edge scanner frame 182 which is horizontally adjustable toward and away from the leading edge of the structural element 170 on adjustment rod 184, and vertically adjustable relative to the leading edge of the structural element 170 on a second adjustment rod 186.

To translate the face sheet scanner 112 chordwise across the structural element 170, it is contemplated that a motor will be encased within the slider 116 to interact with the guide rod 118 via gears or friction wheels. Alternatively, the chordwise action may be achieved by positioning the motor on the forward body part 102 and translating the slider 116 via a cable, drive belt, chain, or screw-drive.

Figure 2:
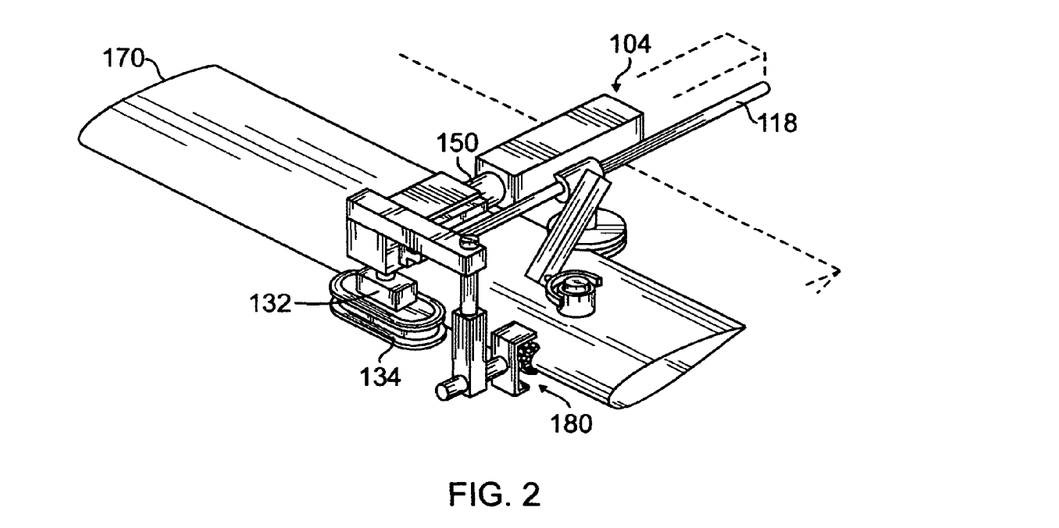
FIG. 2 is a perspective view of the inspection apparatus depicted in FIG. 1 mounted on an airfoil structure of shorter chordlength.

FIG. 2 shows the inspection apparatus 100 of FIG. 1 of the present disclosure mounted on a structural element 170 of shorter chordlength than the chordlength of the structural element 170 shown in FIG. 1. As described previously, the internal spring or compression generating mechanism contained in the rear body part is configured to expand or contract to accommodate chordlength variations. When the internal spring or compression generating mechanism causes the rear body part 104 to translate along the intercostals element 150, the inspection apparatus 100 effectively expands and contracts to accommodate a wide variety of structural element 170 chord lengths, as illustrated in FIGS. 1 and 2.

FIG. 2 shows the inspection apparatus 100 of FIG. 1 of the present disclosure mounted on a structural element 170 of shorter chordlength than the chordlength of the structural element 170 shown in FIG. 1. As described previously, the internal spring or compression generating mechanism contained in the rear body part is configured to expand or contract to accommodate chordlength variations. When the internal spring or compression generating mechanism causes the rear body part 104 to translate along the intercostals element 150, the inspection apparatus 100 effectively expands and contracts to accommodate a wide variety of structural element 170 chord lengths, as illustrated in FIGS. 1 and 2.

Figure 3:
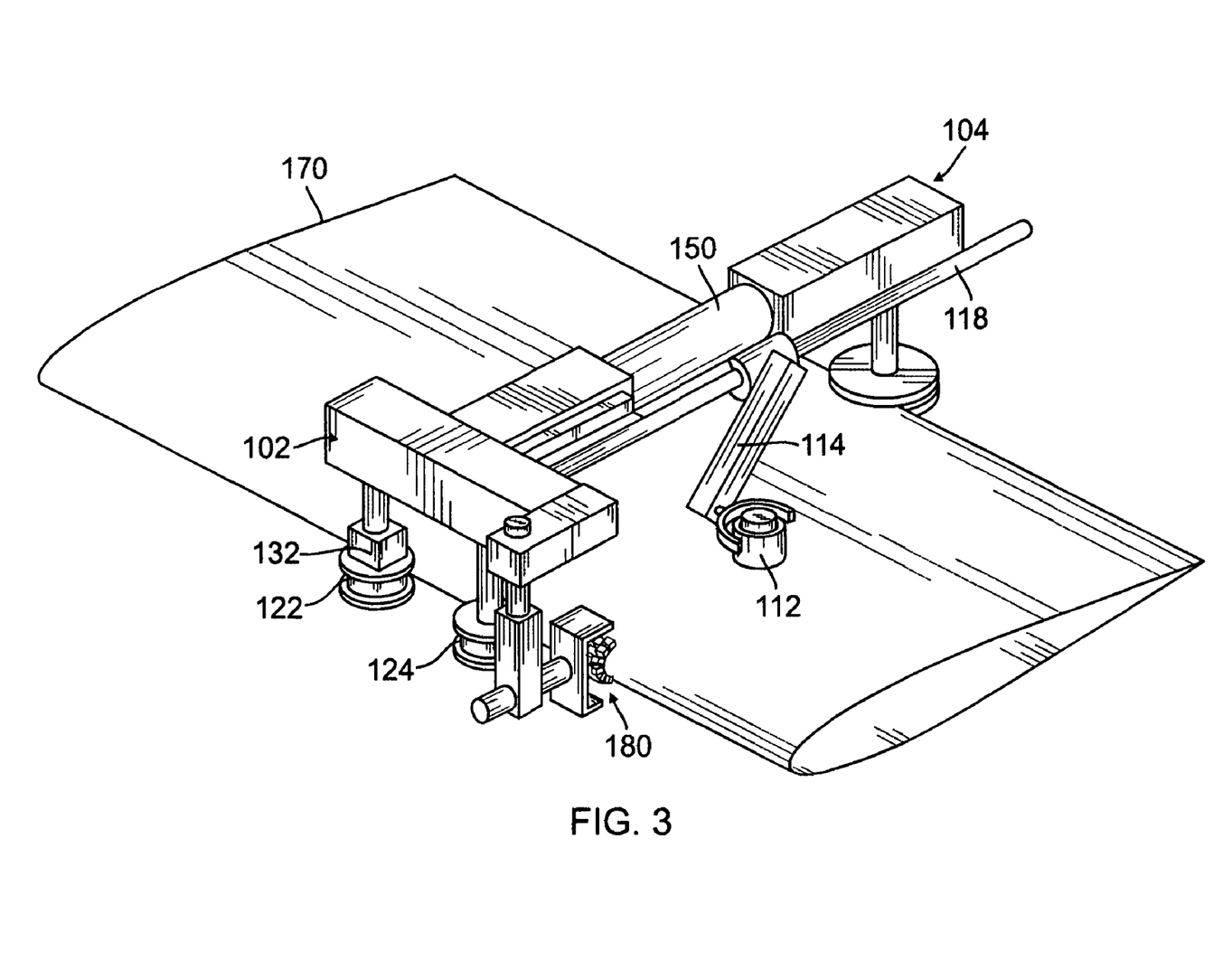
FIG. 3 is a perspective view of a variation of the inspection apparatus depicted in FIG. 1.

FIG. 3 shows a second embodiment of the inspection apparatus 100 of the present disclosure which includes all of the principal elements depicted in FIG. 1, with the addition of a drive wheel 122 operatively coupled to the control motor 132 that replaces the drive track 134 shown in FIG. 1, and a secondary follower wheel 124 displaced spanwise from and carried by the forward body part.

Figure 4:
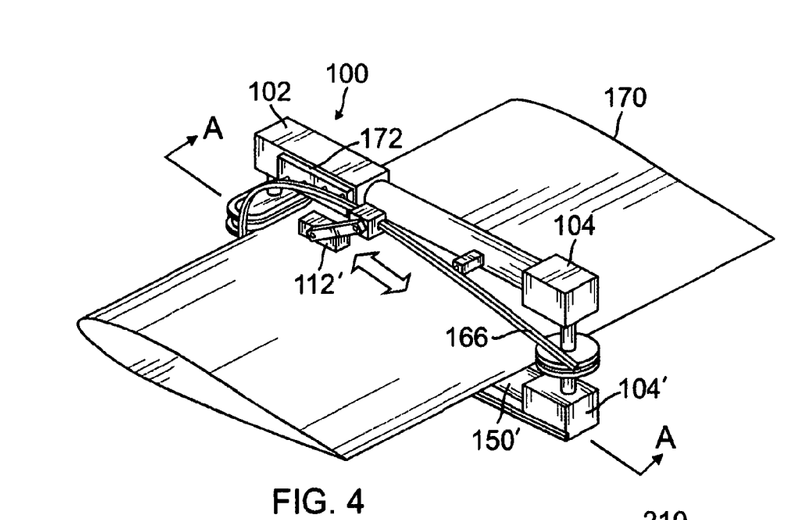
FIG. 4 is a perspective view of another variation of the inspection apparatus of the present disclosure.
Figure 5:
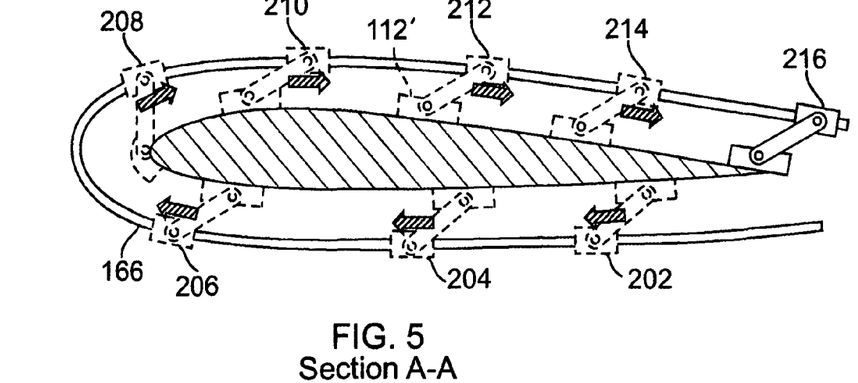
FIG. 5 is a cross-sectional view taken a section line A-A in FIG. 4.

FIGS. 4 and 5 depict another aspect of the inspection apparatus of the disclosure in which scanning of the structural element about nearly 360° is made possible. As seen in FIG. 4, the inspection apparatus 100 includes a bottom structure that mirrors the top structure. The bottom structure includes a forward body part (hidden by the structural element 170 but located below the forward body part 102), a rearward body part 104', and a "intercostal" element 150' positioned below the structural element 170. The two frame members are positioned about, and encompass, the structural element 170. A continuous guide rod 166 supports the slider 116 to which the NDI scanner element 112' is attached. The continuous guide rod 166 extends, with a gradual accurate curvature, from the rearward region to the forward region of the upper frame member, and then with a short radius extends from the forward region of the upper frame member to the forward region of the lower frame member, and then extends toward the rear region of the lower frame member. The slider 166 translates in the same manner as was described in FIGS. 1, 2, and 3.

FIG. 5 is a sectional view of the structural element 170 shown in FIG. 4 with the variant of the inspection apparatus 100 shown in FIG. 4, and depicting the path of travel of the face-sheet scanner 112 as it moves about the airfoil from a first "starting" position 202 (for example, a starting position at the bottom rearward edge of the airfoil) through a series of intermediate positions 204-214 (shown in phantom) where measurements are taken, to a second "ending" position 216 (for example, an ending position at the top rearward edge of the structural element 170).

Figure 6:
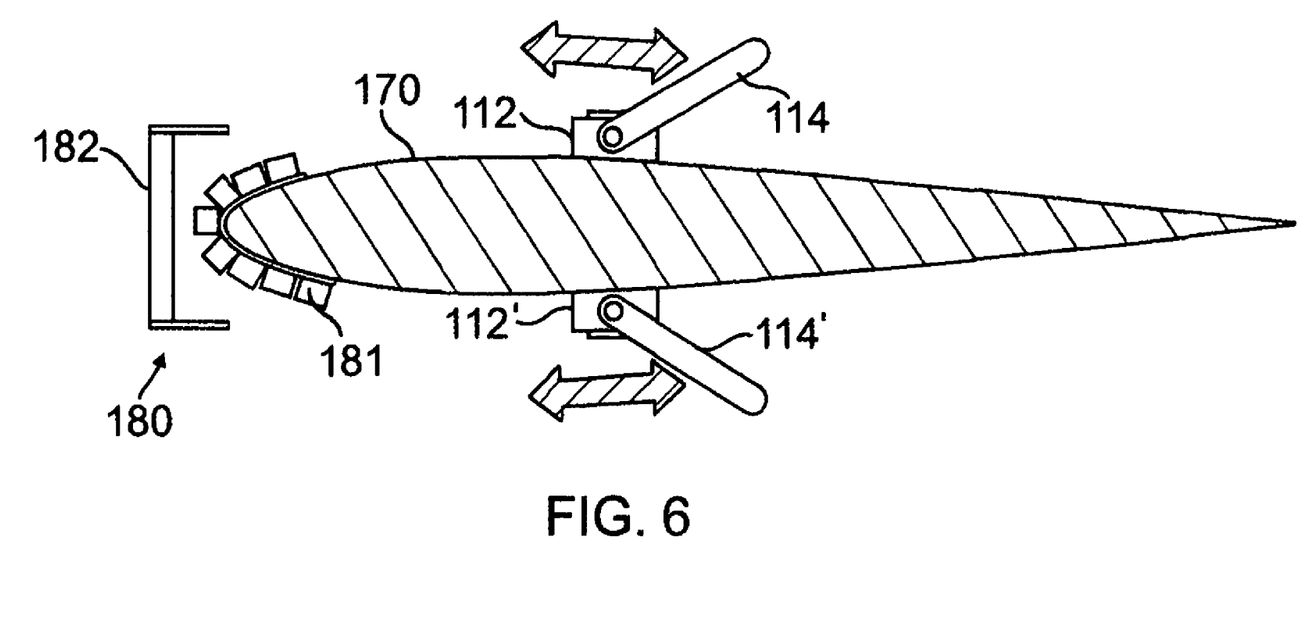
FIG. 6 is a side schematic view of another variation of the inspection apparatus of the disclosure.
Figure 7:
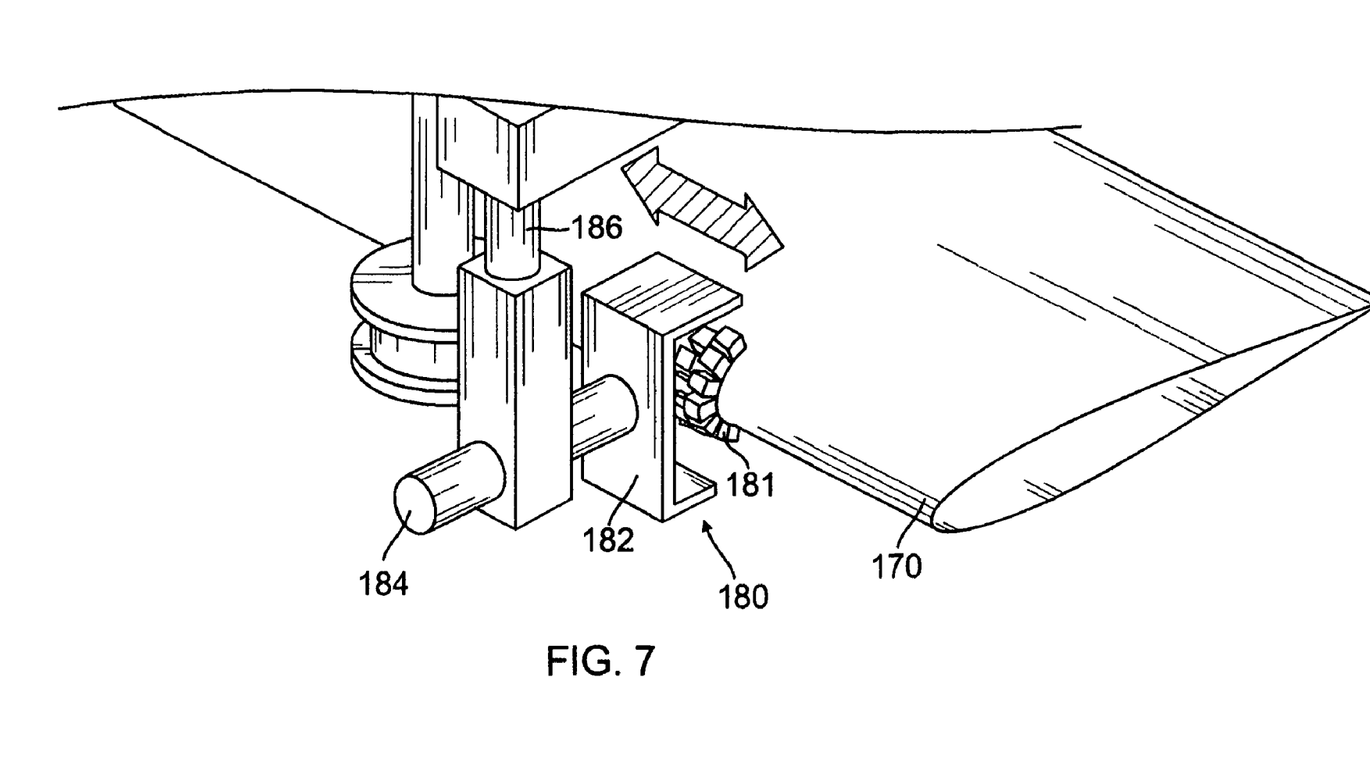
FIG. 7 is a close-up view of the leading edge scanning assembly 180 shown in FIG. 6 disposed at the leading edge of the structural element 170 being inspected.

FIGS. 6 and 7 are schematic illustrations of another aspect of the scanner apparatus in which a pair of NDI scanner elements are carried, respectively, by upper and lower frame members (not shown here) to enable simultaneous inspection of the upper and lower surfaces of the structural element 170. A leading edge scanner array 181, positioned at the leading edge of the structural element 170, can be carried by leading edge scanner frame 182. The leading edge scanner frame 182 can take the form of an expandable bladder, a foam member, or an elastomeric member, that causes the sensors to conform to the leading edge of the structural element 170. Alternatively, the leading edge scanner frame 182 can include a plurality of spring elements disposed between the inner surface of leading edge scanner frame 182 and adjacent surfaces of the leading edge scanner array 181. Other arrangements may also be used, such as a series of pivots or hinges, to align the leading edge sensor array 181. As shown by the arrows in FIG. 5, the face sheet scanner 112 bearing against the upper, lower, leading and trailing surfaces of the structural element 170 can be moved spanwise while the leading edge scanner translates in the chordwise direction as desired.

Data developed by the sensing elements 112 or 112', as well as by the leading edge sensor array and the positional encoding mechanisms, are fed as analog or digital signals to a processor (not shown). The resulting output of the processor can then be fed to a display device, such as a computer-driven display or a CRT, thereby permitting an operator to view results being obtained. In turn, this permits an operator the opportunity to make appropriate adjustments to the scanner apparatus to insure the desired scanning information is obtained.

While the disclosure has been made with reference to a preferred embodiment, it will be understood by those skilled in the art that various changes may be made and equivalents may be substituted for elements thereof without departing from the scope of this disclosure.

The invention claimed is:

1. An apparatus for providing an automated movement of a non-destructive inspection (NDI) sensor over a workpiece surface, comprising:
   a housing having forward and rear portions engaging opposing edges of the workpiece and an elongate member interconnecting the forward and rear portions of the housing,
   a biasing mechanism interacting with an end portion of the elongate member to urge the forward and rear portions toward one another to cause the workpiece to be securely held therebetween,
   an arm coupled to the housing for reversible movement in a first direction along the length of the elongate member and between the forward and rear portions of the housing, the arm supporting the NDI sensor, and
   a drive mechanism carried by said housing for moving the housing in a second direction perpendicular to the first direction over the workpiece, the drive mechanism including at least one friction element engaging a leading edge of the workpiece and a motor supported by the housing for driving the friction element along the one surface.

2. The apparatus of claim 1, wherein the workpiece comprises an element having an airfoil configuration, and the housing further includes a sensor mechanism arranged at the leading edge of the workpiece for making sensing engagement therewith.

3. The apparatus of claim 2, wherein the sensor mechanism arranged at the leading edge of the workpiece comprises an array of sensing elements supported for conformal engagement with the leading edge of the workpiece.

4. The apparatus of claim 1, and wherein the housing is disposed atop one major surface of the workpiece, the housing further including a guide rod mounted to the forward portion, and a slider element slidably engaged with the guide rod for sliding movement therealong, the arm being pivotably coupled to the slider element.

5. The apparatus of claim 4, and further including an encoder wheel carried by the rear portion of the housing and having a portion engagable with the trailing edge of the workpiece, the encoder wheel transferring the biasing force to the workpiece trailing edge.

6. The apparatus of claim 5, wherein the encoder wheel determines the spanwise position of the apparatus on the workpiece.

7. The apparatus of claim 1, and further including a processor mechanism for analyzing data acquired by the NDI sensor and a display device for visually presenting the analyzed data.

8. An apparatus for providing an automated movement of a non-destructive inspection (NDI) sensor about the upper and lower surfaces of a workpiece with a single continuous motion, comprising:
   an upper housing and a lower housing, each housing having forward and rear portions engaging opposing edges of the workpiece, and an elongate member interconnecting the forward and rear portions, a biasing mechanism interacting with an end portion of the elongate member to urge the forward and rear portions toward one another to cause the workpiece to be securely held therebetween, a drive mechanism carried by at least one of said housings for moving the apparatus in a spanwise direction over the workpiece, the drive mechanism including at least one friction element engaging a leading edge of the workpiece and a motor supported by at least one of the housings for driving the friction element along one of the upper or lower surfaces, an elongated guide rod encircling the upper and lower surfaces of the workpiece and being secured to at least one of the housings, a slider element coupled to the guide rod and movable therealong, and driver apparatus for moving the slider element along the guide rod.

9. The apparatus of claim 8, wherein the forward portions of the upper and lower housings are both connected to the drive mechanism.

10. The apparatus of claim 8, and further including an NDI sensor engaging a surface of the workpiece and an elongate arm connected between and to the NDI sensor and the slider element, the NDI sensor being moved along the upper and lower surfaces of the workpiece in a chordwise direction.

11. The apparatus of claim 10, wherein the NDI sensor comprises at least one of a pulse-echo sensor, a shear wave sensor, a resonance sensor, a mechanical impedance sensor, and an eddy current sensor.

12. The apparatus of claim 11, wherein the workpiece comprises an element having an airfoil configuration.

13. An apparatus for providing simultaneous non-destructive inspection (NDI) of upper and lower surfaces of a workpiece, comprising:

an upper housing and a lower housing, each housing including forward and rear portions engaging opposing edges of the workpiece, and an elongate member connecting the forward and rear housing portions, a biasing mechanism interacting with an end of the elongate member to urge the forward and rear portions toward one another to hold the workpiece securely therebetween, a drive mechanism for moving the housing in a spanwise direction over the workpiece, the drive mechanism including a friction element engaging a leading edge surface of the workpiece and a motor for driving the friction element along the edge surface, a guide rail mounted to a portion of the housing and extending in a chordwise direction, an NDI sensor element that is coupled to the guide rail for movement in the chordwise direction, and motion imparting apparatus for moving the NDI sensor element over the respective surface of the workpiece, motor apparatus for driving each of the upper and lower housings over a respective surface of the workpiece, and coupling apparatus for coupling the upper and lower housings together so that the upper and lower housings move simultaneously chordwise over the upper and lower workpiece surfaces.

14. The apparatus of claim 13, wherein the NDI sensor comprises at least one of a pulse-echo sensor, a thru-transmission sensor, a shear wave sensor, a resonance sensor, a mechanical impedance sensor, and an eddy current sensor.

15. The apparatus of claim 13, wherein each of the upper and lower housings include a follower mechanism engaged with the trailing edge of the workpiece, the follower mechanism containing an encoding device to determine the spanwise location of the apparatus on the workpiece.

16. The apparatus of claim 13, and further including a processor mechanism for analyzing data acquired by the NDI sensor, and a display device for visually presenting the analyzed data.

17. The apparatus of claim 13, wherein at least one of the upper and lower housings further includes an encoder wheel supported from the rear portion thereof, the encoder wheel being urged into engagement with the trailing edge of the workpiece in order to determine the spanwise position of the apparatus as it moves along the workpiece.

18. The apparatus of claim 13, and further including a sensor mechanism arranged at the leading edge of the workpiece and making engagement therewith.

19. The apparatus of claim 18, wherein the sensor mechanism comprises an array of NDI sensing elements and a flexible member to which the elements are mounted, the elements being supported by the flexible member for conformal engagement with the leading edge of the workpiece.

* * * * *